(12) United States Patent
Mishima et al.

(10) Patent No.: US 6,758,838 B2
(45) Date of Patent: Jul. 6, 2004

(54) DISPOSABLE UNDERGARMENT

(75) Inventors: Yoshitaka Mishima, Kagawa-ken (JP); Miyuki Ikeda, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 116 days.

(21) Appl. No.: 10/017,967

(22) Filed: Dec. 6, 2001

(65) Prior Publication Data

US 2002/0072727 A1 Jun. 13, 2002

(30) Foreign Application Priority Data

Dec. 8, 2000 (JP) ........................................ 2000-374843

(51) Int. Cl.[7] .............................................. A61F 13/15
(52) U.S. Cl. .............................. 604/385.08; 604/385.19
(58) Field of Search ...................... 604/385.01, 385.08, 604/385.19, 385.21–385.23

(56) References Cited

U.S. PATENT DOCUMENTS

| | | | |
|---|---|---|---|
| 2,468,445 A | | 4/1949 | Hurst |
| 3,532,093 A | | 10/1970 | Lovret |
| 3,828,784 A | | 8/1974 | Zoephel |
| 4,623,342 A | * | 11/1986 | Ito et al. ............... 604/385.23 |
| 4,756,709 A | * | 7/1988 | Stevens ................ 604/385.22 |
| 4,850,990 A | | 7/1989 | Huntoon et al. |
| 4,935,021 A | | 6/1990 | Huffman et al. |
| 5,137,526 A | * | 8/1992 | Coates ....................... 604/391 |
| 5,176,672 A | * | 1/1993 | Bruemmer et al. ..... 604/385.19 |
| 5,224,941 A | | 7/1993 | Simmons |
| 5,304,159 A | * | 4/1994 | Tanji et al. ............ 604/385.19 |
| 5,342,342 A | * | 8/1994 | Kitaoka ................. 604/385.19 |
| 5,344,516 A | * | 9/1994 | Tanji et al. .................. 156/164 |
| 5,630,376 A | * | 5/1997 | Ochi et al. ................... 119/169 |
| 6,406,465 B1 | * | 6/2002 | Otsubo .................. 604/385.01 |
| 6,527,756 B1 | * | 3/2003 | Mishima et al. ....... 604/385.19 |

FOREIGN PATENT DOCUMENTS

| | | |
|---|---|---|
| EP | 1034760 | 9/2000 |
| GB | 2280374 | 2/1995 |
| JP | 2000-14699 | 1/2000 |
| WO | WO 96/34589 | 11/1996 |

* cited by examiner

Primary Examiner—John J. Calvert
Assistant Examiner—Catharine L Anderson
(74) Attorney, Agent, or Firm—Butzel Long

(57) ABSTRACT

A disposable undergarment that includes an elastically stretchable base sheet having transversely opposite side edge portions intended to define leg-holes. Along the side edge portions, the base sheet is folded back onto itself and joined together so that a basis weight of the base sheet is higher in the transversely opposite side edges than in the remaining area of the base sheet and a tensile stress of the base sheet is higher in the transversely opposite side edges than the remaining area of the base sheet.

4 Claims, 9 Drawing Sheets

DISPOSABLE UNDERGARMENT

BACKGROUND OF THE INVENTION

This invention relates to a disposable undergarment for absorption and containment of body excretion.

Japanese Patent Application Publication No. 2000-14699A discloses a disposable undergarment of open-type comprising an elastically stretchable base sheet, a liquid-pervious topsheet smaller than the base sheet and a liquid-absorbent panel disposed between these sheets. The base sheet is composed, in a longitudinal direction, of a front waist region, a rear waist region and a crotch region extending between these waist regions. The crotch region is formed along its transversely opposite side edges with transversely opposite side edge portions curving transversely inward so as to describe circular arcs and intended to define leg-holes. According to the disclosure of the above-identified Publication, the base sheet is formed of elastically stretchable stock material to ensure a good fit of the base sheet around the wearer's torso and thighs and thereby to prevent body excretion from leaking beyond peripheral edges of a waist-hole as well as a pair of leg-holes without any elastic members attached to the undergarment in associated with the waist-hole as well as with the leg-holes.

Generally, it is required for the disposable undergarment absorbing and containing body excretion to ensure the transversely opposite side edge portion intended to define the leg-holes' each having a circumferential dimension smaller than that of the waist-hole's peripheral edge to fit around the wearer's thighs sufficiently to prevent body excretion from leaking through the peripheral edges of the leg-holes. However, the above-identified Publication discloses no measure to improve the fit of the transversely opposite side edge portions intended to define the leg-holes around the wearer's thighs. With the undergarment disclosed therein, a dimension by which the undergarment is stretchable as the undergarment is put on the wearer's body is larger in the area surrounding the wearer's torso than in the transversely opposite side edge portions intended to define the leg-holes surrounding the wearer's thighs and these transversely opposite side edge portions can not fit around the wearer's thighs with sufficiently high stretch stress to ensure a desired leak-barrier effect.

SUMMARY OF THE INVENTION

It is an object of this invention to provide a disposable undergarment that is designed so transversely opposite side edges portions of the undergarment intended to form leg-holes and having elastic stretchability can sufficiently fit around the wearer's thighs to prevent body excretion from leaking through peripheral edges of the leg-holes.

According to this invention, there is provided a disposable undergarment comprising a substantially liquid-impervious base sheet having elastic stretchability, a liquid-absorbent panel attached to an inner surface of the base sheet, a front waist region, a rear waist region and a crotch region extending therebetween, and the crotch region being formed along transversely opposite sides thereof with transversely opposite side edge portions intended to define leg-holes curving transversely inward so as to describe substantially circular arcs.

The base sheet is folded back at least once onto itself along the transversely opposite side edge portions intended to define the leg-holes, a basis weight of the base sheet in the transversely opposite side edge portions intended to define the leg-holes being higher in the transversely opposite side edge portions than in a remaining area of the base sheet, and a tensile stress of the base sheet being higher in the transversely opposite side edge portions than in the remaining area of the base sheet.

According to one embodiment of this invention, a substantially liquid-impervious elasticized cover sheet is placed on a inner surface of the base sheet so as to cover a substantially entire area of the base sheet and has at least one opening being relatively large in the longitudinal direction with a peripheral portion joined to a peripheral portion of the base sheet, and wherein the cover sheet is folded back at least once onto itself and joined together along the transversely opposite side edge portions intended to define the leg-holes so that a basis weight of the cover sheet is higher in the transversely opposite side edge portions intended to define the leg-holes than in a remaining area of the cover sheet and a tensile stress of the cover sheet is higher in the transversely opposite side edge portions than in the remaining area of the cover sheet.

According to another embodiment of this invention, the cover sheet is folded back at least once onto itself along the peripheral edge portion of the opening so that a basis weight of the cover sheet is higher in the peripheral edge portion of the opening than in a remaining area of the cover sheet and a tensile stress of the cover sheet is higher in the peripheral edge portion of the opening than the remaining area of the cover sheet.

According to still another embodiment of this invention, a bulging seam formed on the cover sheet extends in the longitudinal direction in vicinity of a longitudinal center line of the cover sheet and the bulging seam is formed by joining the inner surface of the cover sheet.

DETAILED DESCRIPTION OF THE INVENTION

Details of a disposable undergarment according to this invention will be more fully understood from the description of an open-type diaper given hereunder with reference to the accompanying drawings as one embodiment of this invention.

Figure 1:
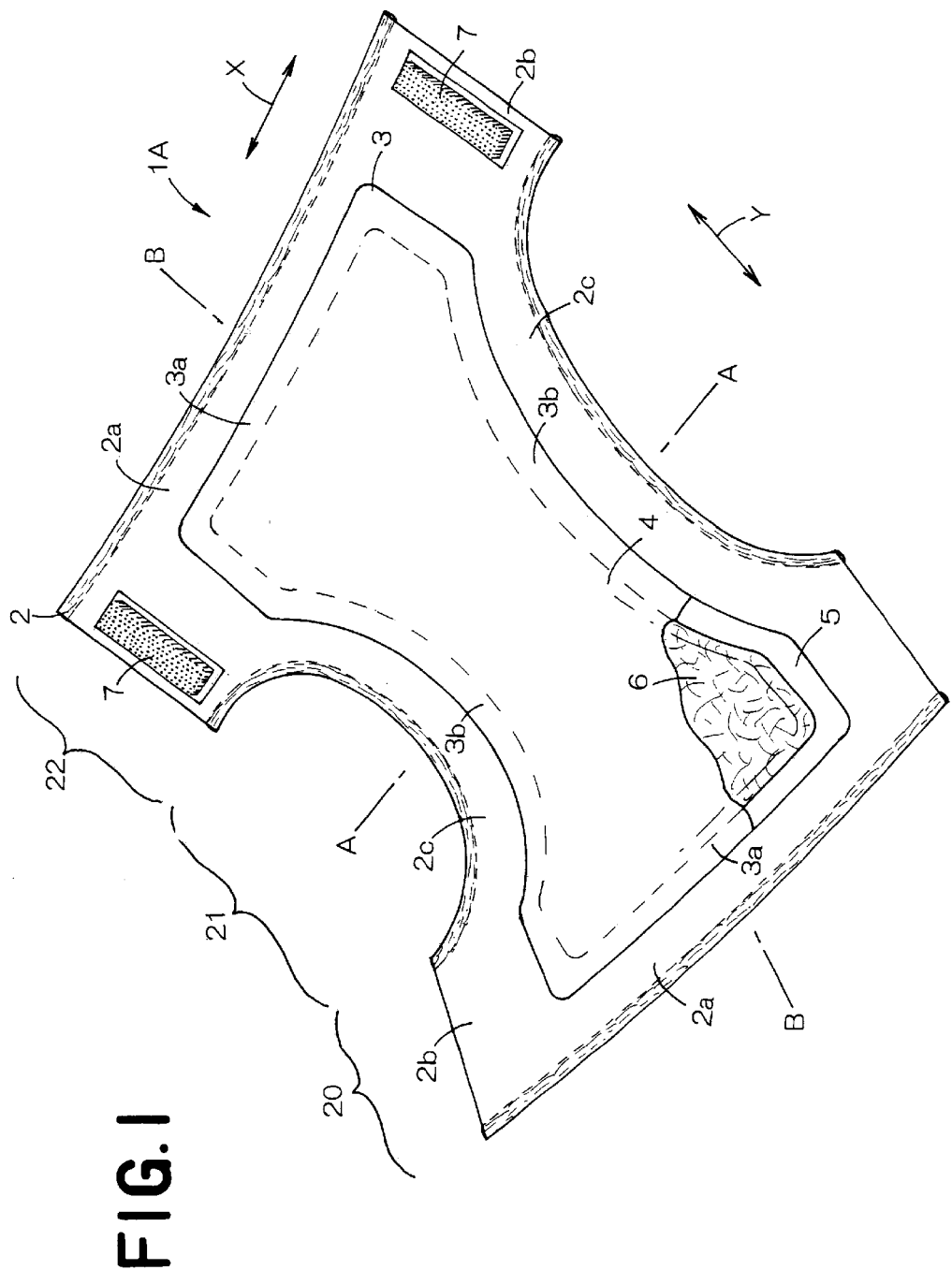
FIG. 1 is a partially cutaway perspective view of a diaper according to this invention from its side facing the wearer's skin.
Figure 2:
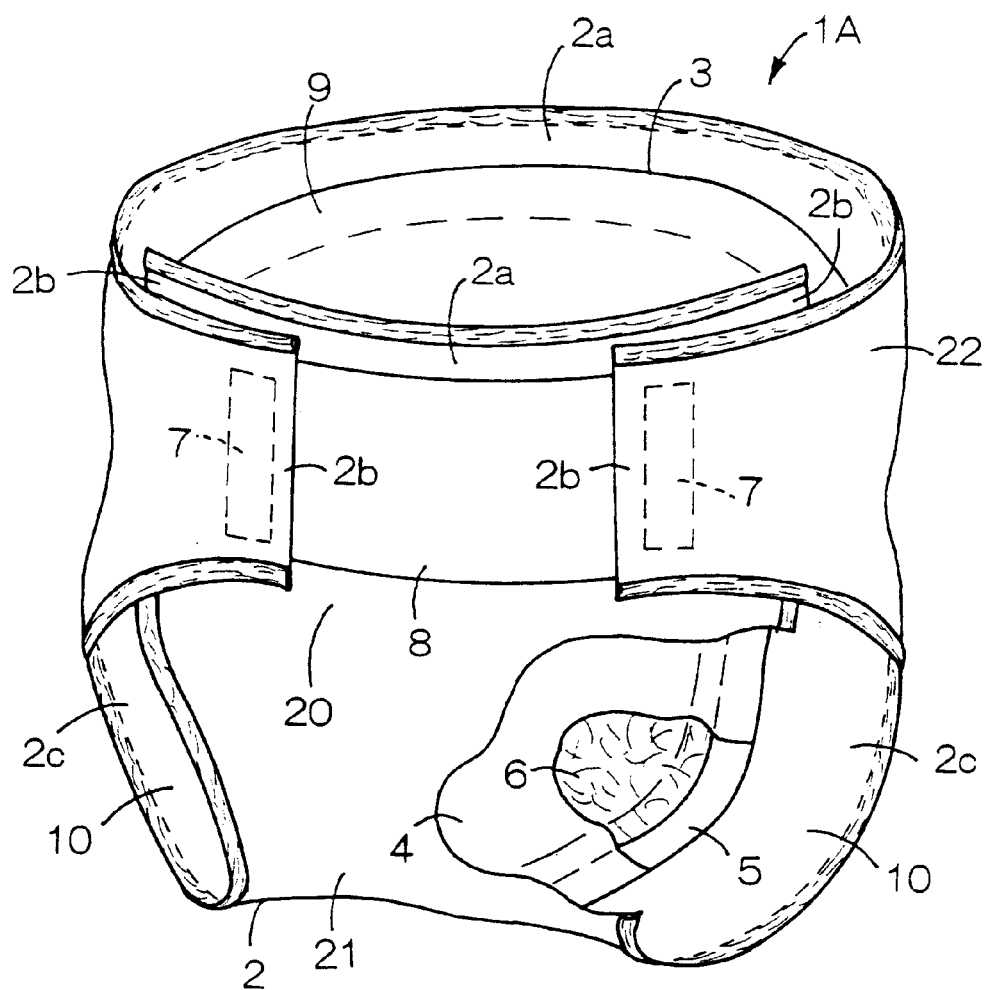
FIG. 2 is a partially cutaway perspective view of the diaper with its front and rear waist regions connected together around the wearer's body.
Figure 3:
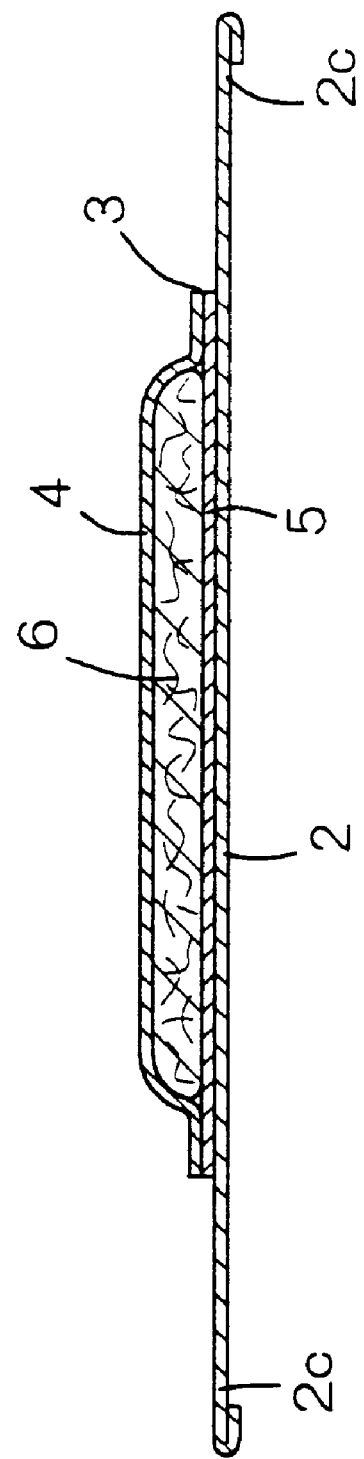
FIG. 3 is a sectional view of the diaper taken along a line A—A in FIG. 1.
Figure 4:
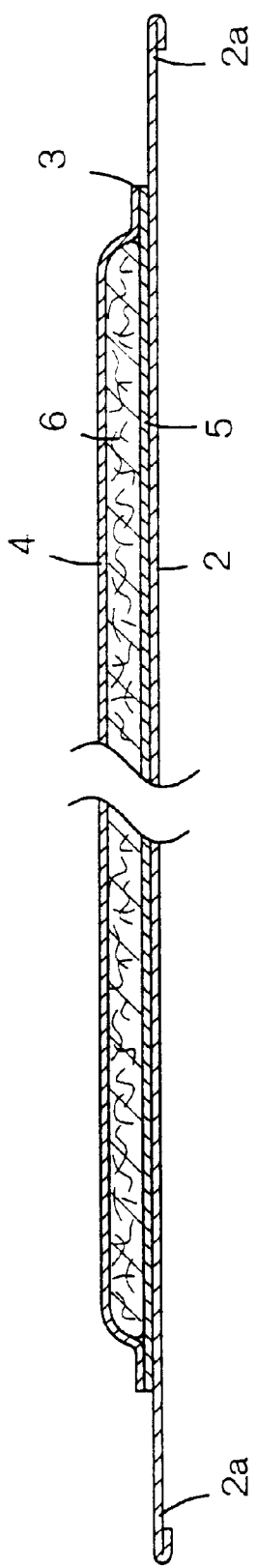
FIG. 4 is sectional view of the diaper taken a line B—B in FIG. 1.

FIG. 1 is a partially cutaway perspective view of the diaper 1A viewed from its inner side, FIG. 2 is partially cutaway perspective view of the diaper 1A with its front and rear waist regions 20, 22 connected to each other around the wearer's body, FIG. 3 is a sectional view of the diaper taken along a line A—A in FIG. 1 and FIG. 4 is a sectional view of the diaper taken along a line B—B in FIG. 1. In FIG. 1, a longitudinal direction is indicated by an arrow Y and a transverse direction is indicated by an arrow X. The surface referred to herein as the inner surface of a base sheet 2, a topsheet 4, a leak-barrier sheet 5 and a cover sheet 11 should be understood to be the surface facing a core 6 and the surface of these sheets 2, 4, 5, 11 referred to herein as the outer surface should be understood to be the surface not facing the core 6.

The diaper 1A comprises the substantially liquid-impervious base sheet 2 and a liquid-absorbent panel 3. The diaper 1A is composed, in the longitudinal direction, of the front waist region 20, the rear waist region 22 and a crotch region 21 extending between these two waist regions 20, 22. The base sheet 2 defines the front and rear waist regions 20, 22 as well as the crotch region 21.

The base sheet 2 is formed of an elastically stretchable fibrous nonwoven fabric. The base sheet 2 is contoured by longitudinally opposite end portions 2a extending in the transverse direction, transversely opposite side edge portions 2b extending in the longitudinal direction along transversely opposite side edges of the front and rear waist regions 20, 22, respectively, and transversely opposite side edge portions 2c extending in the longitudinal direction along transversely opposite side edges of the crotch region 21 so as to define leg-holes. The transversely opposite side edge portions 2c curve inward as seen in the transverse direction substantially in circular arcs.

The panel 3 is shaped in an hourglass which is smaller than that of the base sheet 2 and attached to the inner surface of the base sheet 2 so as to extend in the longitudinal direction. The panel 3 comprises the liquid-pervious topsheet 4, the substantially liquid-impervious leak-barrier sheet 5 and the liquid-absorbent core 6 disposed between the topsheet 4 and the leak-barrier sheet 5. The core 6 is entirely covered with and joined to tissue paper (not shown) and joined to the inner surfaces of the topsheet 4 and the leak-barrier sheet 5 with the tissue paper lying therebetween.

The panel 3 is firmly joined to the base sheet 2 with the leak-barrier sheet 5 lying therebetween. In the panel 3, respective peripheral portions of the topsheet 4 and the leak-barrier sheet 5 extend outward slightly beyond the peripheral edge of the core 6 and the peripheral portions of these sheets 4, 5 are overlaid with each other and joined together.

The base sheet 2 is folded outward back onto itself along its longitudinally opposite end portions 2a and transversely opposite side edge portions 2c and the portions of the base sheet 2 thus overlaid with each other together are intermittently joined to each other. Consequently, a basis weight of the base sheet 2 is higher in these end portions 2a and side edge portions 2c than that in the remaining zone and a tensile stress of the base sheet 2 in these end portions 2a and side edge portions 2c also is higher than that in the remaining zone.

The base sheet 2 is provided on its inner surface with a pair of hook members 7. These hook members 7 are placed at opposite lateral zones of the rear waist region 22. The base sheet 2 is provided on its outer surface with a rectangular loop member 8 which is longer in the transverse direction. Specifically, this loop member 8 is placed on the front waist region 20 and defines a landing zone for the hook members 7.

To wear the diaper 1A, the rear waist region 22 may be placed upon the outer side of the front waist region 20 and the hook members 7 may be engaged with the loop member 8 to connect these waist regions 20, 22 to each other. A waist-hole 9 and a pair of leag-holes 10 are defined as the front and rear waist regions 20, 22 of the diaper 1A are connected to each other in this manner, as seen in FIG. 2. When the diaper 1A is put on the wearer's body, the longitudinally opposite end portions 2a of the base sheet 2 extend in a circumferential direction around the wearer's waist and the transversely opposite side edge portions 2c of the base sheet 2 extend in the circumferential direction around the wearer's thighs, respectively.

In the diaper 1A, the longitudinally opposite end portions 2a as well as the transversely opposite side edge portions 2c respectively have a tensile stress higher than that in the remaining area, so such relatively high tensile stress functions to press the longitudinally opposite end portions 2a and the transversely opposite side edge portions 2c against the wearer's waist and thighs, respectively when being put on the wearer's body. In this way, the longitudinally opposite end portions 2a come in sufficiently close contact with the wearer's waist and the transversely opposite side edge portions 2c come in sufficiently close contact with the wearer's thighs to prevent the body excretion from leaking through the waist-hole as well as through the leg-holes.

In the diaper 1A, it is possible to increase a basis weight and a stretch stress of the longitudinally opposite end portions 2a as well as the transversely opposite side edge portions 2c of the base sheet 2 without attaching separately prepared elastically stretchable members to these end portions 2a and side edge portions 2c. If such elastically stretchable members are attached to these end portions 2a and side edge portions 2c of the base sheet 2, a plurality of gathers are formed along these end and side edge portions 2a, 2c. It is apprehended for the diaper 1A of this invention that such gathers do not form along the end portions 2a and the side edge portions 2c, thus it eliminates the uncomfortable stimulation due to the gathers coming in contact with the wearer's skin.

Figure 5:
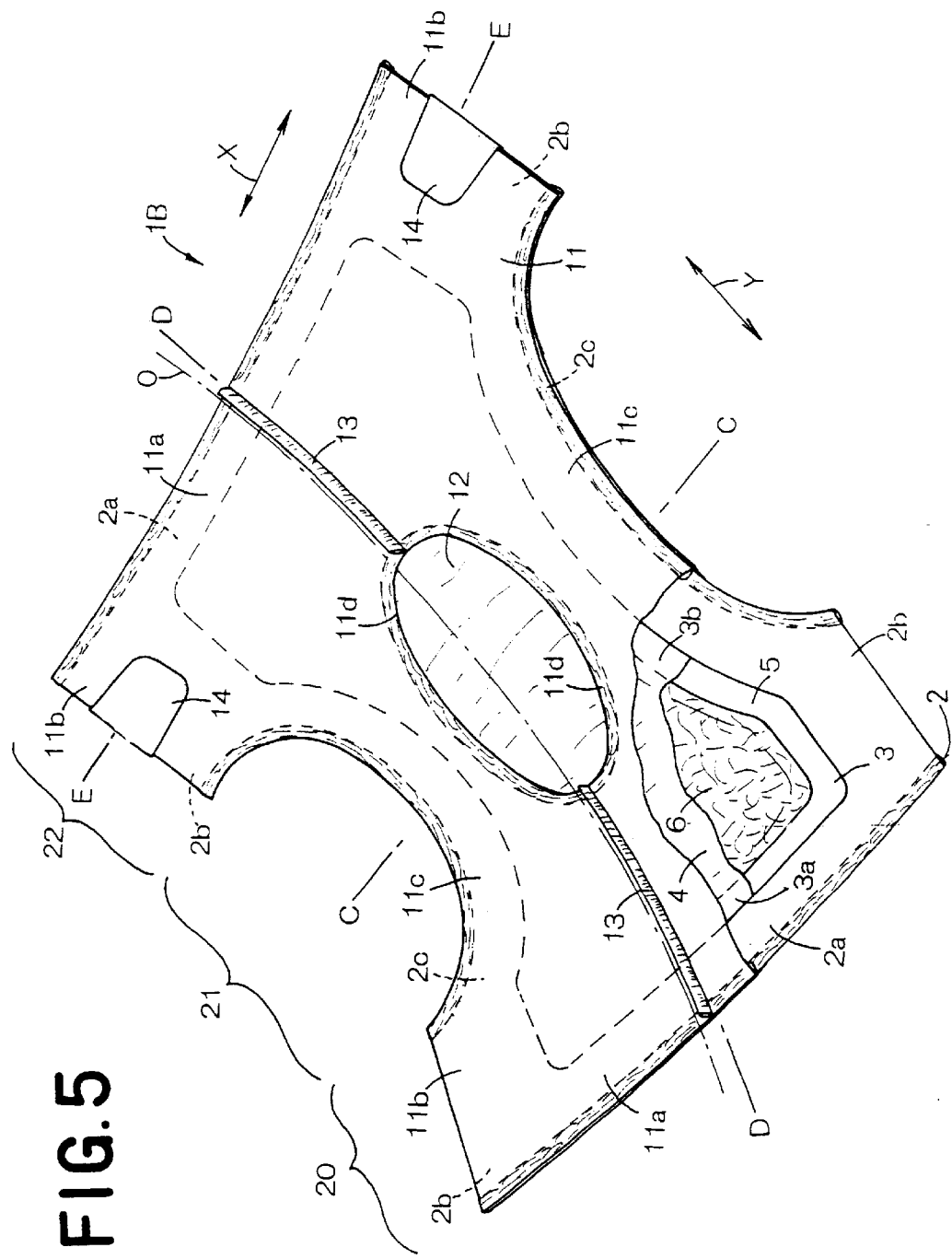
FIG. 5 is a partially cutaway perspective view of another embodiment of the diaper.
Figure 6:
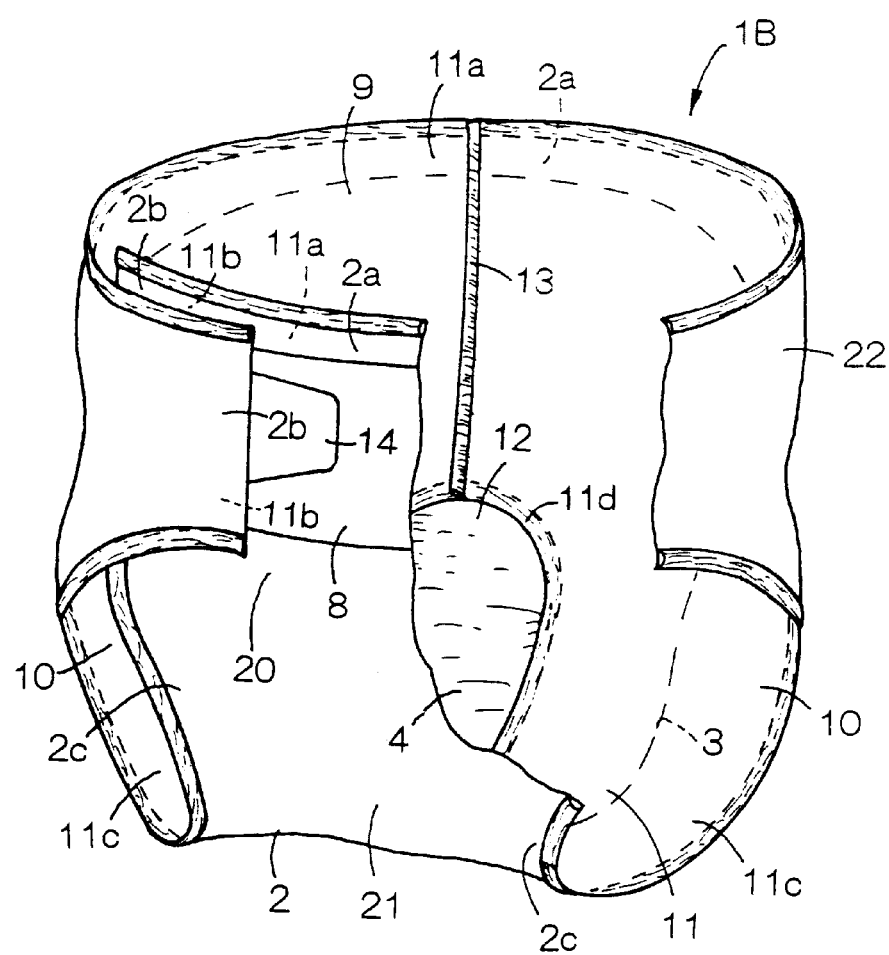
FIG. 6 is a partially cutaway perspective view of this embodiment of the diaper with its front and rear waist regions connected together around the wearer's body.
Figure 7:
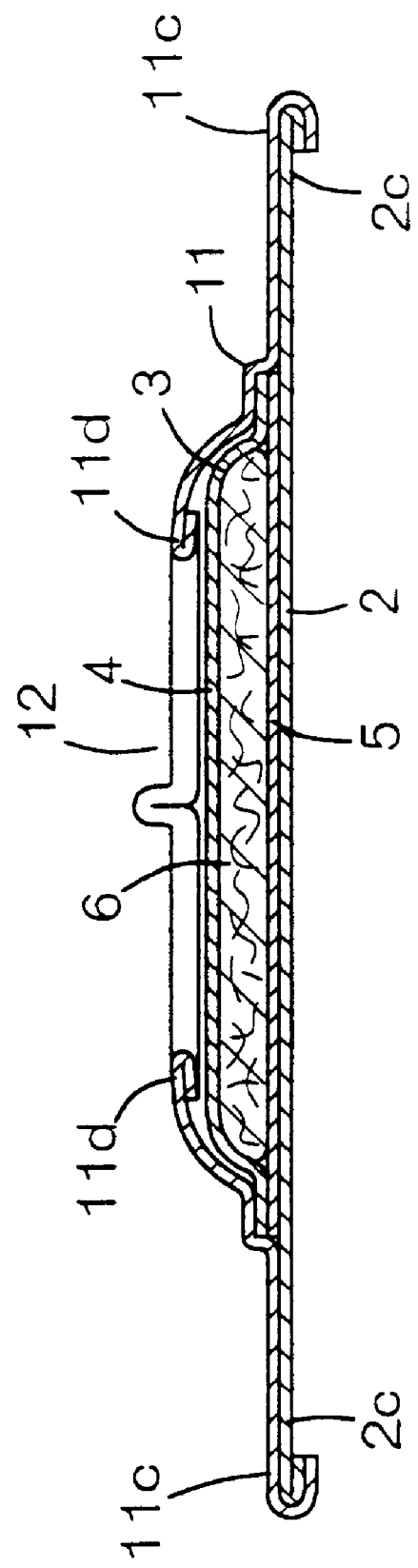
FIG. 7 is a sectional view of the diaper taken along a line C—C in FIG. 5.
Figure 8:
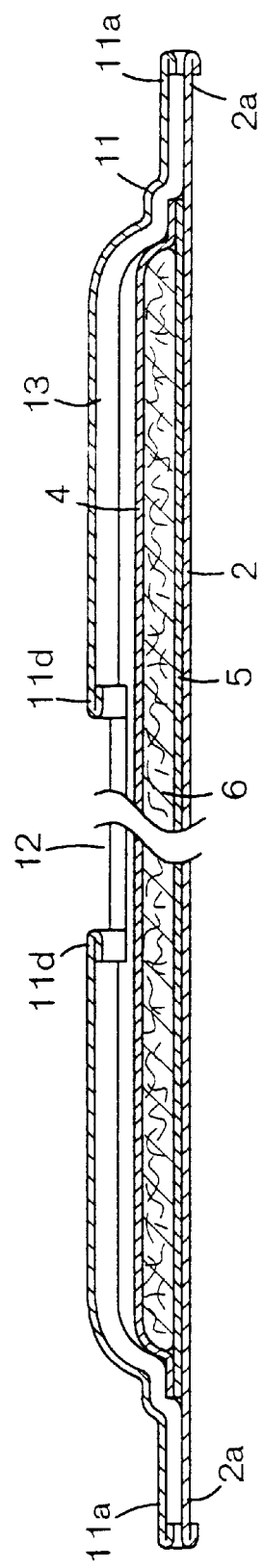
FIG. 8 is a sectional view of the diaper taken along a line D—D in FIG. 5.
Figure 9:
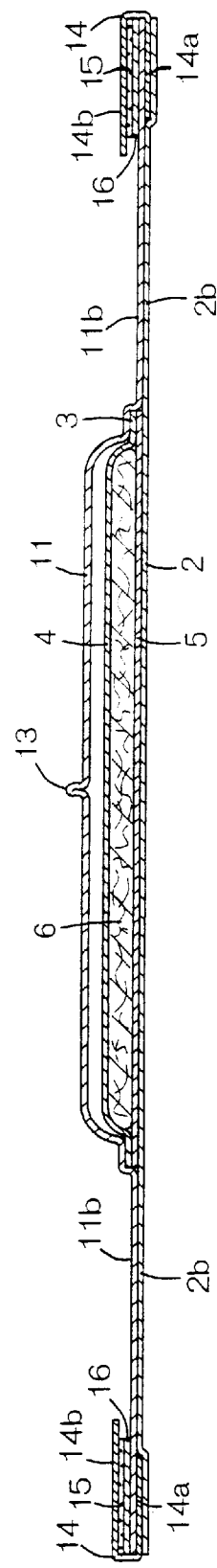
FIG. 9 is a sectional view of the diaper taken along a line E—E in FIG. 5.

FIG. 5 is a partially cutaway perspective view showing another embodiment of the diaper 1B, FIG. 6 is a partially cutaway perspective view showing this embodiment of the diaper 1B with its front and rear waist regions 20, 22 connected together around the wearer's body. FIG. 7 is a sectional view of the diaper taken along a line C—C in FIG. 5, FIG. 8 is a sectional view of the diaper taken along a line D—D in FIG. 5, and FIG. 9 is a sectional view of the diaper taken along a line E—E in FIG. 5. In FIG. 5, a transverse direction is indicated by an arrow X and a longitudinal direction is indicated by an arrow Y.

The diaper 1B is similar to the diaper 1A shown in FIG. 1 in that the diaper 1B comprises a substantially liquid-impervious base sheet 2 and a liquid-absorbent panel 3 attached to the inner surface of the base sheet 2. The diaper 1B is different from the diaper 1A shown in FIG. 1 in an arrangement as will be described.

The base sheet 2 has a substantially liquid-impervious cover sheet 11 attached to the inner surface so as to cover substantially entire area of the base sheet 2. The cover sheet 11 is made of a fibrous nonwoven fabric which is elastically stretchable.

The cover sheet 11 has longitudinally opposite end portions 11a extending in the transverse direction, transversely opposite side edge portions 11b extending in the longitudinal direction along the transversely opposite side portions of the front and rear waist regions 20, 22 and transversely opposite side edge portions 11c extending in the longitudinal direction along the transversely opposite side edge portions of the crotch region 21. The transversely opposite side edges portions 11c curve inward in the transverse direction so as to form substantially circular arcs. In the middle portion of the crotch region 21, the cover sheet 11 has an opening 12 dimensioned to be relatively large in the longitudinal direction and the topsheet 4 constituting the panel 3 is partially surfaced in this opening 12.

The cover sheet 11 is formed with a seam 13 bulging upward. This bulging seam 13 extends in the longitudinal direction in the vicinity of a longitudinal center line O of the cover sheet 11. The bulging seam 13 is formed by joining together the inner surface of the cover sheet 11.

Along a peripheral edge portion 11d of the opening defined by the cover sheet 11, the cover sheet 11 is folded back onto its inner surface and the portions of the cover sheet 11 thus placed upon each are intermittently bonded together. As a result, a basis weight of the cover sheet 11 is higher in the peripheral edge portion 11d of the opening than in the remaining area and a tensile stress of the cover sheet 11 also is higher in the peripheral edge portion 11d of the opening than in the remaining area.

The base sheet 2 and the cover sheet 11 are joined to each other along the respective longitudinally opposite end portions 2a, 11a of these sheets 2, 11, the respective transversely opposite side edge portions 2b, 11b in the front and rear waist regions and the transversely opposite side edge portions 2c, 11c in the crotch region 21. Along the longitudinally opposite end portions 2a, 11b, the base sheet 2 is folded back onto its outer surface and the portions of the base sheet 2 thus placed upon each other are intermittently joined together and the cover sheet 11 also is folded back onto its outer surface and the portions of the cover sheet 11 thus placed upon each other are intermittently joined together. Along the transversely opposite side edge portions 2c, 11c in the crotch region 21, the base sheet 2 and the cover sheet 11 are folded back onto the outer surface of the base sheet 2 and the portions of these sheets 2, 11 thus placed one upon another are intermittently joined together. As a result, a basis weight of these sheets 2, 11 is higher in the longitudinally opposite end portions 2a, 11a as well as the transversely opposite side edge portions 2c, 11c in the crotch region 21 than in the remaining area. A tensile stress of these sheets 2, 11 also is higher in the end portions 2a, 11a and the side edge portions 2c, 11c than in the remaining area.

From the transversely opposite side edge portions 2b, 11b in the rear waist region 22, a pair of tape fasteners 14 extend transversely inward, respectively. Each of the tape fasteners 14 has its proximal end portion 14a disposed and joined between the base sheet 2 and the cover sheet 11. The tape fastener 14 has a free end portion 14b coated with pressure-sensitive adhesive 15. The tape fastener 14 is adapted to be provisionally, i.e., detachably joined by means of pressure-sensitive adhesive to a plastic tape strip 16 attached to the outer surface of the cover sheet 11. A target tape strip 17 which is relatively elongate in the transverse direction, is attached to the outer surface of the base sheet 2 in the front waist region 20.

To wear the diaper 1B, the rear waist region 22 is placed upon the outer surface of the front waist region 20 and the free end portions 14b of the respective tape fasteners 14 are fixed to the target tape strip 17 by a means of pressure-sensitive adhesive 15 to connect these waist regions 20, 22 to each other.

In the diaper 1B, the longitudinally opposite end portions 2a, 11a as well as the transversely opposite side edge portions 2c, 11c respectively have a tensile stress higher than that in the remaining area, so such relatively high tensile stress functions to press the longitudinally opposite end portions 2a, 11a and the transversely opposite side edge portions 2c, 11c against the wearer's waist and thighs, respectively. In this way, the longitudinally opposite end portions 2a, 11a come in sufficiently close contact with the wearer's waist and the transversely opposite side edge portions 2c, 11c come in sufficiently close contact with the wearer's thighs to prevent the body excretion from leaking through the waist-hole as well as through the leg-holes.

In the cover sheet 11, if the peripheral edge portion 11d of the opening is distorted to form pleats or gathers therealong, any amount of body excretion such as urine or loose feces held on the topsheet 4 would flow along these pleats or gathers and cling to the wearer's skin. However, the diaper 1B according to this invention well overcomes this problem by its unique arrangement such that the basis weight of the cover sheet 11 is higher in the peripheral edge portion of the opening than the remaining area and the tensile stress also is higher in the peripheral edge portion than the remaining area. Specifically, the peripheral edge portion 11d of the opening is resistant to formation of those pleats or gathers and therefore the anxiety that the body excretion might flow the peripheral edge portion 11d of the opening and cling to the wearer's skin can be completely avoided or minimized.

In the diaper 1B, the bulging seam 13 extending on the cover sheet 11 in the longitudinal direction is fitted in the recess of the wearer's buttock as the diaper 1B is worn. In this way, the bulging seam 13 limits movement of the diaper 1B in the transverse direction and thereby prevents the diaper 1B from shifting sideways.

The base sheet 2 and the cover sheet 11 may be formed from an elastically stretchable hydrophobic fibrous non-woven fabric obtained by the melt blown or spun bond process. The component fiber of such elastic stretchable nonwoven fabric may be stretchable fibers obtained by melting and spinning a thermoplastic elastomer resin. The elastically stretchable fibrous nonwoven fabric may be a composite nonwoven fabric synthetic resin such as polypropylene, polyethylene or polyester bonded to at least one surface of the hydrophobic fibrous nonwoven fabric.

The topsheet 4 may be formed of a hydrophilic fibrous nonwoven fabric or finely apertured plastic film. The leak-barrier sheet 5 may be formed of a hydrophobic fibrous nonwoven fabric or a liquid-impervious plastic film.

The nonwoven fabric used to form the topsheet 4 and the leak-barrier sheet 5 may be selected from a group consisting of those obtained by spun lacing, needle punching, melt blowing, thermal bonding, spun bonding, chemical bonding and air-through processes. The component fiber of such nonwoven fabric may be selected from a group consisting of polyolefine-, polyester- and polyamide-fiber, and core-sheath type conjugated fiber or side-by-side type conjugated fiber of polyethylene/polypropylene or polyethylene/polyester.

The core 6 comprises a mixture of fluff pulp and super-absorbent polymer particles or a mixture of fluff pulp, superabsorbent polymer particles and thermoplastic synthetic resin fiber compressed to a desired thickness. The superabsorbent polymer may be selected from a group consisting of starch-based polymer, cellulose-based polymer and synthetic polymer.

With the diaper 1B shown by FIG. 5, the panel 3 is formed from the liquid-absorbent core 6 which may be directly attached to the base sheet 2 without need for the topsheet 4 or without need for the leak-barrier sheet 5. In this case, the core 6 should preferably comprise a compressive fibrous web having restored elasticity containing superabsorbent polymer particles dispersed and retained in fiber interstices of this fibrous web and shape-stabilized by compressing the fibrous web to a desired thickness. The component fiber of such fibrous web may be selected from a group consisting of polyolefine-based fiber such as polypropylene or polyethylene, polyester-based fiber such as polyethylene terephthalate, polyamide-based fiber such as nylon 66 or nylon 6, acryl-based fiber, and cellulose-based fiber such as pulp, rayon or acetate.

With the diaper 1B shown in FIG. 5, the cover sheet 11 may have two openings. In this case, these openings should preferably be formed in the front waist region 20 and the rear waist region 22, respectively, so that these openings may be located in coincidence with the urinary organs and the anus, respectively.

Joining between the base sheet 2 and the leak-barrier sheet 5, and between the topsheet 4 and the leak-barrier sheet 5, fixing of the cover sheet 11 to the base sheet 2, and attachment of the core 6 may be achieved by using hot melt adhesive or heat welding technique such as heat-sealing or sonic-sealing.

This invention is applicable not only to the open-type diaper but also to the pants-type diaper having its front and rear waist regions previously connected to each other.

In the disposable undergarment according to this invention is the basis weight of the undergarment in its transversely opposite side edge portions intended to define the leg-holes is higher than in the remaining area and the tensile stress of the undergarment also is higher in these portions than in the remaining area. This feature is effective to provide a good fit of the undergarment around the wearer's thighs. Even if a dimension by which the undergarment is stretchable as it is worn is larger in its waist regions than in the transversely opposite side edge portions intended to define the leg-holes, the relatively high tensile stress of these side edge portions sufficiently presses the undergarment around the wearer's thighs to reliably prevent the body excretion from leaking through the leg-holes' peripheral edge portions.

In the embodiment of the undergarment provided with the cover sheet, the peripheral edge portion of the opening is well resistant to formation of pleats or gathers. This feature eliminates an apprehension that the body excretion might flow along these pleats or gathers and cling to the wearer's skin. An anxiety that the body excretion might cling to the peripheral edge portion of the opening is also minimized. In the embodiment of the article formed on the cover sheet with the bulging seam, the bulging seam is fitted in the recess of the wearer's buttock and limits movement of the undergarment in the transverse direction to prevent the article from sliding sideways.

What is claimed is:

1. A disposable undergarment comprising:
   a substantially liquid-impervious base sheet having an inner surface;
   a liquid-absorbent panel attached to the inner surface of said base sheet;
   a front waist region;
   a rear waist region; and
   a crotch region extending between the front waist region and the rear waist region,
   said crotch region having transversely opposite sides, said transversely opposite sides of the crotch region including transversely opposite side edge portions configured to define leg-holes curving transversely inward so as to describe arcs,
   said base sheet being folded back at least once onto itself along said transversely opposite side edge portions configured to define the leg-holes without any intermediate element positioned between portions of the base sheet that are folded back onto itself,
   said base sheet having a basis weight in said transversely opposite side edge portions configured to define the leg-holes that is higher than a basis weight in a remaining area of said base sheet,
   said base sheet having a tensile stress that is higher in said transversely opposite side edge portions than a tensile stress in the remaining area of said base sheet,
   said disposable undergarment further comprising a substantially liquid-impervious cover sheet placed on said liquid-absorbent panel and on sheet, said cover sheet having an elastic stretchability and at least one opening that is elongated in an inner surface of said base sheet so as to cover a substantially entire area of said liquid-absorbent panel and said base said longitudinal direction with a peripheral portion thereof joined to a peripheral portion of said base sheet, said cover sheet further being folded back at least once onto itself and joined together along said transversely opposite side edge portions configured to define the leg-holes so that a basis weight of said cover sheet is higher in said transversely opposite side edge portions configured to define the leg-holes that a basis weight in a remaining area of said cover sheet and a tensile stress of said cover sheet is higher in said transversely opposite side edge portions configured to define the leg-holes than a tensile stress in the remaining area of said cover sheet.

2. The disposable undergarment according to claim 1, wherein said cover sheet is folded back at least once onto itself along the peripheral edge portion of the at least one opening so that a basis weight of said cover is higher in said peripheral edge portion of the at least one opening than a basis weight in a remaining area of said cover sheet and a tensile stress of said cover is higher in said peripheral edge portion of the at least one opening than a tensile stress in the remaining area of said cover sheet.

3. The disposable undergarment according to claim 2, wherein a bulging seam is formed on said cover sheet, the bulging seam extending in a longitudinal direction in a vicinity of a longitudinal center line of said cover sheet and said bulging seam being formed by joining portions of the inner surface of said cover sheet together.

4. The disposable undergarment according to claim 1, wherein said base sheet includes an outer surface opposed to the inner surface and said base sheet is folded back at least once onto itself along said transversely opposite side edge portions so that portions of the outer surface of said base sheet contact one another.

* * * * *